(12) United States Patent
Murakami et al.

(10) Patent No.: US 11,162,123 B2
(45) Date of Patent: Nov. 2, 2021

(54) GLUTAMINE SYNTHETASE REACTION AND METHOD FOR QUANTIFYING AMMONIA UTILIZING THE SAME

(71) Applicant: ARKRAY, Inc., Kyoto (JP)

(72) Inventors: Masaki Murakami, Kyoto (JP); Takehiro Funamoto, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 16/058,170

(22) Filed: Aug. 8, 2018

(65) Prior Publication Data
US 2019/0048373 A1    Feb. 14, 2019

(30) Foreign Application Priority Data
Aug. 10, 2017   (JP) .............. JP2017-155476

(51) Int. Cl.
| | | |
|---|---|---|
| *C12P 13/14* | (2006.01) | |
| *C12Q 1/25* | (2006.01) | |
| *C12Q 1/32* | (2006.01) | |
| *C12Q 1/54* | (2006.01) | |
| *C12N 9/12* | (2006.01) | |
| *C12Q 1/48* | (2006.01) | |
| *C12N 9/00* | (2006.01) | |
| *C12N 9/04* | (2006.01) | |
| *C12Q 1/00* | (2006.01) | |

(52) U.S. Cl.
CPC ............ *C12P 13/14* (2013.01); *C12N 9/0006* (2013.01); *C12N 9/1205* (2013.01); *C12N 9/93* (2013.01); *C12Q 1/008* (2013.01); *C12Q 1/25* (2013.01); *C12Q 1/32* (2013.01); *C12Q 1/485* (2013.01); *C12Q 1/54* (2013.01); *C12Y 101/01049* (2013.01); *C12Y 207/01001* (2013.01); *C12Y 603/01002* (2013.01); *G01N 2333/904* (2013.01); *G01N 2333/91215* (2013.01)

(58) Field of Classification Search
None
See application file for complete search history.

(56) References Cited

U.S. PATENT DOCUMENTS 5,916,761 A  *  6/1999  Koga ................ C12Q 1/48
                                                435/21
2018/0112250 A1    4/2018  Funamoto et al.

FOREIGN PATENT DOCUMENTS

| EP | 0881301 A1 | 12/1998 |
|---|---|---|
| JP | S62-003800 A | 1/1987 |
| JP | S62-142272 A | 6/1987 |
| JP | H07-051094 A | 2/1995 |
| JP | H09-285297 A | 11/1997 |
| JP | 2000-253898 A | 9/2000 |
| JP | 2018-068278 A | 5/2018 |

OTHER PUBLICATIONS

New additional English Machine Translation of JP 2000-253898A; Application published Sep. 19, 2000 (of record).*
English Machine Translation of JP 2000-253898A; Application published Sep. 19, 2000 (of record). (Year: 2000).*
Office Action issued in corresponding European Patent Application No. 18187959.4 dated Oct. 12, 2018.
Woolfolk et al., "Regulation of Glutamine Synthetase: Reversible Dissociation and Inactivation of Glutamine Synthetase from *Escherichia coli* by the Concerted Action of EDTA and Urea," Archives of Biochemistry and Biophysics, 122: 174-189 (1967).
Office Action issued in corresponding European Patent Application No. 18187959.4 dated Sep. 26, 2019.
Extended European Search Report issued in corresponding European Patent Application No. 18187959.4 dated Oct. 12, 2018.
Office Action issued in corresponding European Patent Application No. 18187959.4 dated May 29, 2020.
Office Action issued in corresponding Japanese Patent Application No. 2017-155476 dated Apr. 27, 2021.

* cited by examiner

*Primary Examiner* — Soren Harward
*Assistant Examiner* — Paul D Pyla
(74) *Attorney, Agent, or Firm* — Morgan, Lewis & Bockius LLP

(57) ABSTRACT

A reagent for glutamine synthetase reaction comprising a chelating agent and glutamine synthetase, and a reagent for quantification of ammonia comprising a chelating agent, ATP, glutamic acid, glutamine synthetase, glucose, an oxidized NAD compound, ADP-dependent hexokinase, and glucose-6-phosphate dehydrogenase, are provided.

15 Claims, 2 Drawing Sheets

GLUTAMINE SYNTHETASE REACTION AND METHOD FOR QUANTIFYING AMMONIA UTILIZING THE SAME

TECHNICAL FIELD

The present invention relates to a technique in the field of biochemistry using enzymatic reaction, more specifically, an analysis technique using enzymatic reaction.

BACKGROUND ART

Glutamine synthetase (GST) is an enzyme that converts glutamic acid to glutamine using ammonia, and utilized for matter production, analysis techniques, and the like using the enzymatic reaction. For example, techniques in which ammonia or ATP in a sample is measured using the amount of substrate consumed by glutamine synthetase as an index are known (Patent Documents 1 and 2). Glutamine synthetase is known to be inhibited by L-methionine sulfoximine or phosphinothricin (glufosinate).
[Patent Document 1] JP 62-3800 A
[Patent Document 2] JP 62-142272 A

SUMMARY OF THE INVENTION

One aspect of the present invention is to provide a reagent for more efficiently allowing the reaction of glutamine synthetase to proceed. Another aspect of the present invention is to provide a reagent for more efficiently allowing the reaction of glutamine synthetase to proceed without being affected by inhibitors, thereby enabling more accurate quantification of ammonia.

The present inventors developed a novel method for quantification of ammonia using glutamine synthetase, and made a patent application (JP Published Patent Application No. 2018-68278, and US Published Patent Application No. 2018-0112250).

Further, as a result of continuation of the study aiming at achievement of an increased accuracy, the present inventors found that, in quantification of ammonia using glutamine synthetase, the presence of calcium in the reaction system causes variation in measurement results on the amount of ammonia. The presence of calcium in the reaction system is thought to be originated from, for example, the calcium contained in a sample or a reagent, or eluted from a measurement device or parts thereof. As a result of further study for elucidation of the cause of the variation, the present inventors found that the activity of glutamine synthetase in the first step is inhibited by calcium. The present inventors then found that, by addition of a chelating agent to the reaction system, the inhibition of glutamine synthetase activity in the first step can be suppressed, and that ammonia can therefore be quantified accurately without being affected by calcium.

One embodiment of the present invention provides a method for carrying out glutamine synthetase reaction, comprising carrying out glutamine synthetase reaction in a reaction system containing ammonia, adenosine triphosphate (ATP), and L-glutamate, wherein said reaction system further contains a chelating agent. Here, the chelating agent may include a compound containing not less than four carboxyl groups in its molecular structure. The chelating agent may be selected from the groups consisting of ethylenediaminetetraacetic acid (EDTA), diethylene triamine-N,N,N',N'',N''-pentaacetic acid (DTPA), and trans-1,2-diaminocyclohexane-N,N,N',N'-tetraacetic acid (CyDTA).

Another embodiment of the present invention provides a method for quantifying ammonia, comprising providing an ammonia-containing sample, carrying out glutamine synthetase reaction using the ammonia-containing sample by the method as described above to generate adenosine diphosphate (ADP), and quantifying ammonia based on the amount of ADP produced or the amount of reaction product produced from the ADP. Here, the quantification of ammonia may be carried out by allowing glucose and ADP-dependent hexokinase to act on the ADP to produce glucose-6-phosphate, and then allowing glucose-6-phosphate dehydrogenase to act on the glucose-6-phosphate and an oxidized nicotinamide adenine dinucleotide (NAD) compound to produce a reduced NAD compound, followed by quantifying the reduced NAD compound. A coloring agent may be reacted with the reduced NAD compound to produce a pigment, and then the pigment is quantified to achieve the quantification of ammonia.

Another embodiment of the present invention provides a reagent kit for glutamine synthetase reaction, comprising a chelating agent and glutamine synthetase. Here, the chelating agent may be a compound containing not less than four carboxyl groups in its molecular structure. The chelating agent may be selected from the group consisting of EDTA, DTPA, and CyDTA.

Another embodiment of the present invention provides a reagent kit for glutamine synthetase reaction, comprising a chelating agent, adenosine triphosphate (ATP), glutamic acid, and glutamine synthetase.

Another embodiment of the present invention provides a reagent kit for quantification of ammonia comprising a chelating agent, adenosine triphosphate (ATP), glutamic acid, and glutamine synthetase. The reagent kit may further comprise glucose, an oxidized NAD compound, an ADP-dependent hexokinase, and glucose-6-phosphate dehydrogenase. The reagent kit may further comprise a coloring agent and an electron carrier.

According to the present invention, the reaction of glutamine synthetase can be allowed to proceed efficiently without being affected by calcium in the reaction system, and analysis or matter production using glutamine synthetase can be more efficiently carried out. In particular, when quantification of ammonia in a sample is carried out using the reaction of glutamine synthetase, ammonia can be accurately quantified without being affected by calcium in the sample.

EMBODIMENTS FOR CARRYING OUT THE INVENTION

Figure 1:
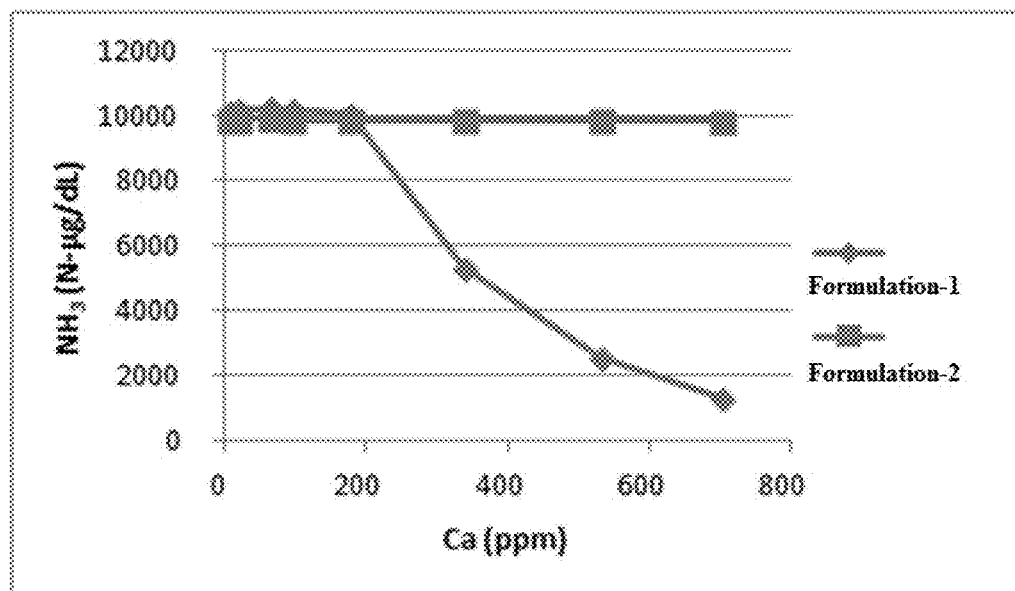
FIG. 1 is a graph illustrating the relationship between the calcium concentration and the measured value of ammonia in an ammonia measurement system (liquid reaction system) using glutamine synthetase. "◇" represents no addition of EDTA, and "□" represents addition of EDTA.

In the method according to one embodiment of the present invention, glutamine synthetase reaction is carried out in a reaction system containing a chelating agent in addition to ammonia, adenosine triphosphate (ATP), and L-glutamate.
<Reaction by Glutamine Synthetase>

As shown by the Reaction Formula (1), the reaction by glutamine synthetase is a reaction in which ammonia ($NH_3$), ATP, and L-glutamate are reacted with each other to produce ADP, orthophosphate, and L-glutamine.

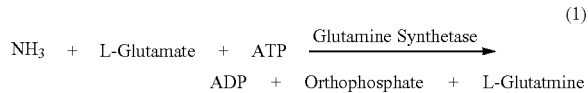
(1)

As long as the above reaction can be catalyzed, the origin of the glutamine synthetase is not limited. A naturally existing glutamine synthetase may be used, or a recombinant glutamine synthetase may be used.
<Chelating Agent>

The type of the chelating agent is not limited as long as it can produce a chelating effect on calcium ions. The chelating agent may include a compound having not less than two carboxyl groups in its molecular structure, and a compound having not less than four carboxyl groups in its molecular structure.

More specific examples of the chelating agent include the following compounds, and salts thereof:

mono- or polyalkylene polyamine polycarboxylic acids . . . ethylenediaminetetraacetic acid (EDTA), 1,6-hexamethylenediamine-N,N,N',N'-tetraacetic acid (HDTA), triethylenetetramine hexaacetic acid (TTHA), diethylenetriamine-N,N,N',N'',N''-pentaacetic acid (DTPA), hydroxyethylethylenediaminetriacetic acid (EDTA-OH), N,N-bis(2-hydroxybenzyl)ethylenediamine-N,N-diacetic acid (HBED), and the like;

polyaminoalkane polycarboxylic acids . . . diaminopropanetetraacetic acid (Methyl-EDTA), trans-1,2-diaminocyclohexane-N,N,N',N'-tetraacetic acid (CyDTA), 1,2-bis(o-aminophenoxy)ethane tetraacetic acid (BAPTA), and the like;

polyaminoalkanol polycarboxylic acids . . . diaminopropanol tetraacetic acid (DPTA-OH) and the like;

hydroxyalkylether polyamine polycarboxylic acids . . . glycol ether diaminetetraacetic acid (GEDTA) and the like;

alkylimino polycarboxylic acids . . . hydroxyethyliminodiacetic acid (HIDA), iminodiacetic acid (IDA), and the like; and nitrilopolycarboxylic acids . . . nitrilotriacetic acid (NTA) and the like. Among these, EDTA, CyDTA, DTPA, GEDTA, TTHA, and Methyl-EDTA are more preferred.

The amount of the chelating agent used is not limited as long as the chelating effect can be produced so that the calcium present in the reaction system does not affect the activity of glutamine synthetase. Although the amount cannot be defined as a certain specific value since it may vary depending on the type of the chelating agent, the type of the reaction system, the calcium concentration, and the like, it may be not less than 0.5 mM, not less than 1 mM, not less than 2 mM, or not less than 5 mM. The upper limit of the amount is not limited, and, taking into account the solubility and the economic efficiency, it may be not more than 200 mM, not more than 100 mM, not more than 60 mM, or not more than 20 mM.

In the reaction system of glutamine synthetase, from the viewpoint of efficiently allowing the reaction, at least one of magnesium ion ($Mg^{2+}$) and manganese ion ($Mn^{2+}$) may be allowed to be present as a catalyst(s) besides the chelating agent, glutamic acid, ammonia, and ATP. The concentration of $Mg^{2+}$ and $Mn^{2+}$ is, for example, 1 to 100 mM. Since $Mg^{2+}$ and $Mn^{2+}$ may be chelated due to the chelating agent, the concentration of $Mg^{2+}$ and $Mn^{2+}$ is preferably higher than that of the chelating agent.

In the reaction system, a buffer, a surfactant, and/or the like may be allowed to be present.

The reaction conditions are not limited as long as the reaction of glutamine synthetase can be allowed to proceed, and may be conventionally used conditions. For example, the reaction may be carried out at 10 to 50° C., or 15 to 40° C., for 1 minute to 3 hours.
<Reagent Kit for Glutamine Synthetase Reaction>

The reagent kit for glutamine synthetase reaction according to one embodiment of the present invention contains the above chelating agent and glutamine synthetase.

The reagent kit for glutamine synthetase reaction according to one embodiment of the present invention may be in the form of a kit containing the chelating agent together with glutamic acid, ATP, glutamine synthetase, and/or the like.
<Method for Quantifying Ammonia>

The method for quantifying ammonia according to one embodiment of the present invention is a method in which glutamine synthetase reaction is carried out using an ammonia-containing sample, and ammonia in the sample is quantified based on the amount of ammonia consumed by the reaction. The method is characterized in that the chelating agent described above is allowed to be present in the glutamine synthetase reaction system in addition to ammonia, adenosine triphosphate (ATP), and L-glutamate.

The ammonia-containing sample is not limited as long as it contains ammonia. Examples of the ammonia-containing sample include those containing ammonia produced by enzymatic reaction, and those containing ammonia produced or released by a chemical reaction (for example, hydrolysis). More specific examples of the ammonia-containing sample include blood, serum, urine, and saliva.

As shown by the above Reaction Formula (1), ammonia is consumed by glutamine synthetase reaction to produce each of ADP and orthophosphate in the same amount (equal moles) as the amount of ammonia. Thus, ammonia can be quantified by measuring the amount of ADP or orthophosphate, or the amount of a product of a reaction using the ADP or the orthophosphate.

The method for measuring the amount of the product of the reaction using the orthophosphate produced is not limited as long as it is a measurement method using the orthophosphate produced by the glutamine synthetase reaction. Examples of the method include the method using purine nucleoside phosphorylase and purine nucleosides as described in Patent Document 2.

The method for measuring the amount of the product of the reaction using the ADP produced is not limited as long as it is a measurement method using the ADP produced by the glutamine synthetase reaction. Examples of the method include the method using ADP as a coenzyme together with kinase and its substrate, as described in Patent Document 1.

Examples of embodiments of the method for measuring the amount of the product of the reaction using ADP include the following method.

First, glucose and ADP-dependent hexokinase are reacted with the ADP produced by the glutamine synthetase reaction. More specifically, as shown by the Reaction Formula (2), by allowing ADP-dependent hexokinase (ADP-HK) to act on ADP and D-glucose, glucose-6-phosphate (G6P) and AMP (adenosine monophosphate) are produced.

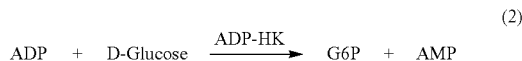

(2)

Subsequently, an oxidized NAD (nicotinamide adenine dinucleotide) compound and glucose-6-phosphate dehydrogenase are allowed to act on the glucose-6-phosphate produced by the reaction of Reaction Formula (2). More specifically, as shown by the Reaction Formula (3), glucose-6-phosphate dehydrogenase (G6PDH) is allowed to act on the glucose-6-phosphate and oxidized NAD ($NAD^+$) to produce reduced NAD (NADH) and D-glucono-1,5-lactone-6-phosphate (6-phosphogluconolactone).

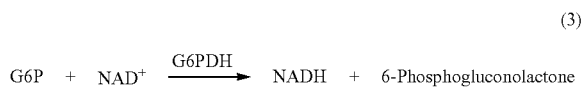

(3)

The NAD compound is not limited to the NAD (nicotinamide adenine dinucleotide) described above, and examples of the NAD compound also include thio-NAD (thionicotinamide adenine dinucleotide), NADP (nicotinamide adenine dinucleotide phosphate), and thio-NADP (thionicotinamide adenine dinucleotide phosphate).

As described above, by allowing glucose-6-phosphate dehydrogenase to act on glucose-6-phosphate and the oxidized NAD compound, a reduced NAD compound is produced. By quantifying the reduced NAD compound (for example, NADH) produced, quantification of ammonia can be carried out. Examples of such a method include a method in which ammonia is quantified by quantifying the reduced NAD compound itself, and a method in which ammonia is quantified by quantifying a pigment obtained by reacting the reduced NAD compound with a coloring agent. For example, in the former method, the electric current value observed upon the production of the reduced NAD compound may be measured, or the amount of increase in the absorbance (340 nm) derived from the reduced NAD compound produced may be measured. In the latter method, the amount of increase in the absorbance derived from the pigment due to the production of the pigment may be measured. Here, since the amount of increase in the absorbance at the particular wavelength (340 nm) absorbed by the reduced NAD compound is in a proportional relationship with the ammonia concentration, or the amount of increase in the absorbance at a particular wavelength absorbed by the produced pigment is in a proportional relationship with the ammonia concentration, quantification of ammonia can be carried out by measuring the absorbance at the particular wavelength.

From the viewpoint of visual identification of the color tone, and from the viewpoint of obtaining a high measurement accuracy even in a case where the ammonia concentration is low, the method in which ammonia is quantified by quantifying a pigment obtained by reacting the reduced NAD compound with a coloring agent may be used.

Alternatively, the quantification of ammonia may be carried out by measuring the reflectance of a test paper obtained by attaching the produced pigment on a base material such as filter paper. For example, a test paper may be obtained by impregnating a base material with a liquid containing a substrate, enzyme, and the like to be used for quantification of ammonia, and then an ammonia-containing sample may be attached to the test paper, followed by measuring the reflectance of the area to which the ammonia-containing sample is attached.

In one example of the method for quantifying ammonia by quantification of a pigment, an electron carrier diaphorase (DI) is allowed to act on the produced reduced NAD compound NADH and a coloring agent tetrazolium violet (TV). As a result, formazan dye is produced as shown in the Reaction Formula (4), resulting in an increase in the absorbance at 560 nm.

(4)

The coloring agent is not limited as long as a pigment is produced by reaction with a reduced NAD compound, that is, as long as a pigment is produced by receiving an electron(s) from a reduced NAD compound. Examples of the coloring agent include tetrazolium compounds.

The tetrazolium compound is not limited as long as the compound has a tetrazole ring. The compound may be a compound having cyclic substituents at two or more positions in the tetrazole ring. The compound may be a compound having cyclic substituents at three or more positions in the tetrazole ring. In a case where the tetrazolium compound has cyclic substituents at two or more positions in the tetrazole ring, the cyclic substituents may be positioned at 2-position and 3-position in the tetrazole ring. In a case where the tetrazolium compound has cyclic substituents at three or more positions in the tetrazole ring, the cyclic substituents may be positioned at 2-position, 3-position, and 5-position in the tetrazole ring. Examples of each cyclic substituent include a benzene ring that may have a substituent(s) (benzene ring-structure substituent), a thienyl group that may have a substituent(s), and a thiazoyl group that may have a substituent(s).

Examples of the tetrazolium compound having cyclic substituents at 2-position, 3-position, and 5-position in the tetrazole ring include 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 2-(2-methoxy-4-nitrophenyl)-3-(4-nitrophenyl)-5-(2,4-disulfophenyl)-2H-tetrazolium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitrophenyl)-5-phenyl-2H-tetrazolium salt], 2,3-diphenyl-5-(4-chlorophenyl)tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, and 2,5-diphenyl-3-(p-tolyl)tetrazolium salt.

The tetrazolium compound may also be a compound having benzene ring-structure substituents at two positions and another kind of cyclic substituent at one position in the tetrazole ring. Examples of such a compound include 2,3- diphenyl-5-(2-thienyl)tetrazolium salt, 2-benzothiazoyl-3-(4-carboxy-2-methoxyphenyl)-5-[4-(2-sulfoethylcarbamoyl)phenyl]-2H-tetrazolium salt, 2,2'-dibenzothiazoyl-5,5'-bis[4-di(2-sulfoethyl)carbamoylphenyl]-3,3'-(3,3'-dimethoxy-4,4'-biphenylene)ditetrazolium salt, and 3-(4,5-dimethyl-2-thiazoyl)-2,5-diphenyl-2H-tetrazolium salt.

The tetrazolium compound may also be a compound having benzene ring-structure substituents at two positions and an acyclic substituent at one position in the tetrazole ring. Examples of such a compound include 2,3-diphenyl-5-cyanotetrazolium salt, 2,3-diphenyl-5-carboxytetrazolium salt, 2,3-diphenyl-5-methyltetrazolium salt, and 2,3-diphenyl-5-ethyltetrazolium salt.

Among the tetrazolium compounds described above, compounds having three cyclic substituents may be used. Compounds having three benzene ring-structure substituents and an electron-withdrawing functional group(s) may be used. 2-(4-Iodophenyl)-3-(2,4-dinitrophenyl)-5-(2,4-disulfophenyl)-2H-tetrazolium salt may be used.

Examples of the electron carrier include diaphorase, phenazine methosulfate, methoxyphenazine methosulfate, and dimethylaminobenzophenoxadinium chloride (Meldola Blue). Among the electron carriers, diaphorase may be used.

The reactions of Reaction Formulae (1) to (3) or the reactions of Reaction Formulae (1) to (4) may be carried out at once in the same reaction system.

In the quantification method of the present embodiment, the reaction temperature may be from 10° C. to 50° C., from 15° C. to 40° C., or from 20° C. to 30° C. The reaction time may be from 1 minute to 60 minutes, from 2 minutes to 30 minutes, or from 5 minutes to 15 minutes.

In the quantification method of the present embodiment, a buffer may be used for adjusting the pH of the ammonia-containing sample to a pH suitable for enzymatic reaction (for example, to a pH of from 6.0 to 9.0). The pH of the buffer may be from 6.0 to 9.0, or from 6.0 to 8.0. Examples of the buffer include Good's buffers such as N-tris(hydroxymethyl)methyl-2-aminoethanesulfonic acid (TES) and N,N-bis(2-hydroxyethyl)-2-aminoethanesulfonic acid (BES); phosphate buffer; imidazole acid buffer; Tris buffer; and glycine buffer.

In the quantification method of the present embodiment, a component(s) other than the components described above may be added to the ammonia-containing sample, if necessary. Examples of the other component(s) include surfactants, antiseptics, and stabilizers.

[Reagent Kit for Quantification of Ammonia]

One embodiment according to one embodiment of the present invention relates to reagent kit for quantification of ammonia.

The reagent kit for quantification of ammonia may include the chelating agent, glutamine synthetase, ATP, and glutamic acid. In cases where the amount of ammonia is quantified based on ADP or orthophosphate produced by glutamine synthetase reaction, the reagent kit may also include a reagent for measuring the amount of ADP or orthophosphate.

In cases where ammonia is quantified based on the amount of orthophosphate produced by glutamine synthetase reaction, the reagent kit may also include, for example, purine nucleoside phosphorylase and purine nucleosides as described in Patent Document 2.

In cases where ammonia is quantified based on the amount of ADP produced by glutamine synthetase reaction, the reagent kit may also include, for example, kinase and its substrate as described in Patent Document 1.

The reagents may be individually contained in a reagent kit such that the reagents can be mixed together upon use, or a part or all of the reagents may be preliminarily mixed.

In one embodiment of the present invention, a reagent kit for carrying out the reactions of Reaction Formulae (1) to (3), or a reagent kit for carrying out the reactions of Reaction Formulae (1) to (4), is/are provided.

Specific examples of the reagent kit include a reagent kit for quantification of ammonia containing the chelating agent, glutamine synthetase, ATP, and glutamic acid, and also glucose, an oxidized NAD compound, ADP-dependent hexokinase, and glucose-6-phosphate dehydrogenase. Examples of the reagent kit include a reagent kit for quantification of ammonia further containing a coloring agent and an electron carrier.

In cases where ammonia is quantified in a solid phase by using a test paper, the reagents may be placed on the test paper in a state where all reagents are mixed together, and may then be stored in a dry state. These reagents may be individually added onto the test paper, or may be preliminarily mixed and then be added onto the test paper at once.

In cases where the quantification of ammonia is carried out in a liquid phase, the reagents may be mixed together immediately before the reaction. The reagents may be divided into several groups, and the reagents in each group are preliminarily mixed together. The groups are then mixed with each other immediately before use.

Examples of such a reagent kit for quantification of ammonia include a kit comprising: a first reagent containing glucose; and a second reagent containing glutamine synthetase, ADP-dependent hexokinase, and glucose-6-phosphate dehydrogenase; wherein ATP, L-glutamic acid, and an oxidized NAD compound are each independently contained in at least one of the first reagent or the second reagent.

In this case, the ATP, L-glutamic acid, and oxidized NAD compound may be contained in the first reagent from the viewpoint of avoiding reaction of a substrate with an enzyme in a reagent.

In the quantification reagent kit of the present embodiment, the first reagent may further contain a coloring agent, and the second reagent may further contain an electron carrier from the viewpoint of quantifying a pigment obtained by reacting the reduced NAD compound with the coloring agent to quantify ammonia.

EXAMPLES

Embodiments of the present invention are described below more concretely by referring to Examples. However, embodiments of the present invention are not limited to the embodiments of the following Examples.

Example 1: Study in Liquid System

Reagents were prepared according to the formulations shown in Table 1. Reagent A was mixed with a sample immediately before the reaction, and then reagent B was added to the resulting mixture to perform the reaction. The ammonia concentration was measured based on the increase in the absorbance at 340 nm during the period of 300 seconds after the beginning of the reaction. To the sample, calcium was added at various concentrations (180, 340, 530, or 700 ppm). The liquid volumes of the reagents were as follows: reagent A, 140 µL; reagent B, 35 µL; sample, 10 µL.

FIG. 1 is a graph illustrating the relationship between the calcium concentration and the measured value of ammonia in an ammonia measurement system (liquid reaction system)

using glutamine synthetase. "◇" represents no addition of EDTA, and "☐" represents addition of EDTA. As a result, as shown in FIG. 1, it was found that the measured value of ammonia decreases dependently on the calcium concentration. In contrast, it was found that, when EDTA is added to the reaction system, the measured value of ammonia does not change dependently on the calcium concentration.

Figure 2:
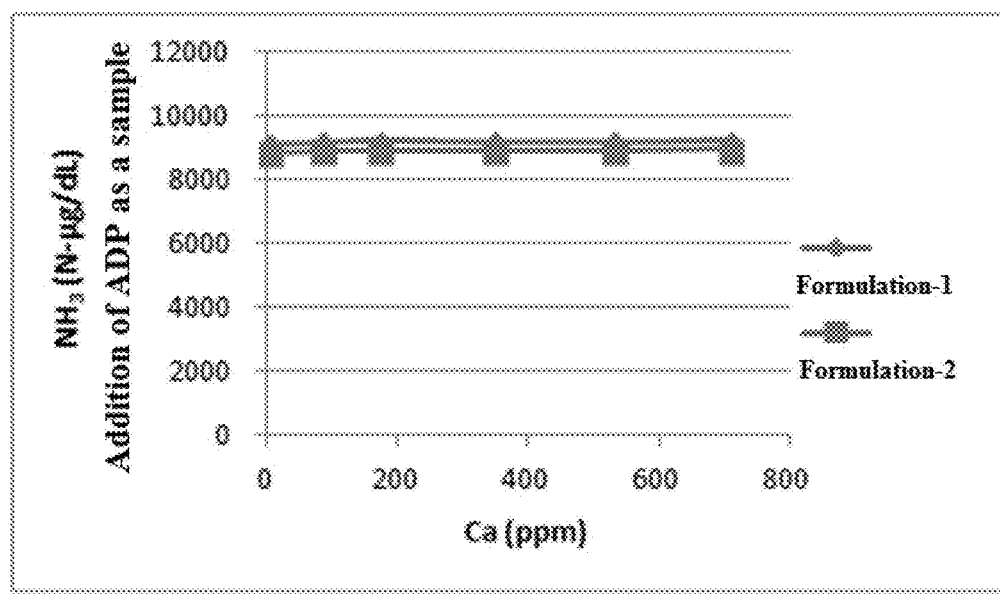
FIG. 2 is a graph illustrating the relationship between the calcium concentration and the measured value of ammonia in an ammonia measurement system (liquid reaction system) using glutamine synthetase, wherein ADP was added as a sample to the reaction system. "◇" represents no addition of EDTA, and "□" represents addition of EDTA.

Subsequently, in what step calcium affects the ammonia measurement reaction was investigated. FIG. 2 is a graph illustrating the relationship between the calcium concentration and the measured value of ammonia in an ammonia measurement system (liquid reaction system) using glutamine synthetase, wherein ADP was added as a sample to the reaction system. "◇" represents no addition of EDTA (formulation-1), and "☐" represents addition of EDTA (formulation-2). Since ADP is a substrate of ADP-dependent hexokinase, the effect of calcium in the sample on the reactions of enzymes excluding glutamine synthetase can be investigated. The addition of ADP to the reaction system resulted in disappearance of the effect of calcium as shown in FIG. 2. Similarly, each of G6P and NADH was added as a sample to the reaction system to investigate the reaction using G6P or NADH as a substrate. As a result, no effect of calcium was found. It was thus found that calcium affects glutamine synthetase in the first step of the ammonia measurement reaction. It was further confirmed that reaction in a solid phase shows a result similar to that in the case of the reaction in the liquid phase on inhibition of the glutamine synthetase activity.

TABLE 1

|  | Formulation-1 | Formulation-2 |
|---|---|---|
| Reagent A | | |
| TES/NaOH pH = 8.0 (mM) | 150.00 | 150.00 |
| NAD+ (mM) | 3.00 | 3.00 |
| L-Glutamate (mM) | 12.00 | 12.00 |
| MgCl2 (mM) | 10.00 | 10.00 |
| EDTA (mM) | 0.00 | 2.00 |
| G6PDH (U/mL) | 8.00 | 8.00 |
| ADP-HK (U/mL) | 3.00 | 3.00 |
| GST (U/mL) | 5.00 | 5.00 |
| Reagent B | | |
| TES/NaOH pH = 8.0 (mM) | 150.00 | 150.00 |
| Glucose (mM) | 15.00 | 15.00 |
| ATP (mM) | 10 | 10 |

Example 2: Study in Solid Phase

Reagents were prepared according to the formulations shown in Table 2. After mixing the components, a base material was impregnated therewith. After drying the base material, a test liquid (10,000 N-μg/dL aqueous ammonia solution supplemented with 0, 10, 30, 60, or 80 ppm calcium) was added thereto, followed by allowing the reaction to proceed at room temperature for 300 seconds and then measuring the reflectance (ΔR). By calculating the difference (ΔR) between the reflectance R of the sample to which calcium was not added and the reflectance R of each sample to which calcium was added, the effect of calcium in the ammonia measurement system can be investigated.

Figure 3:
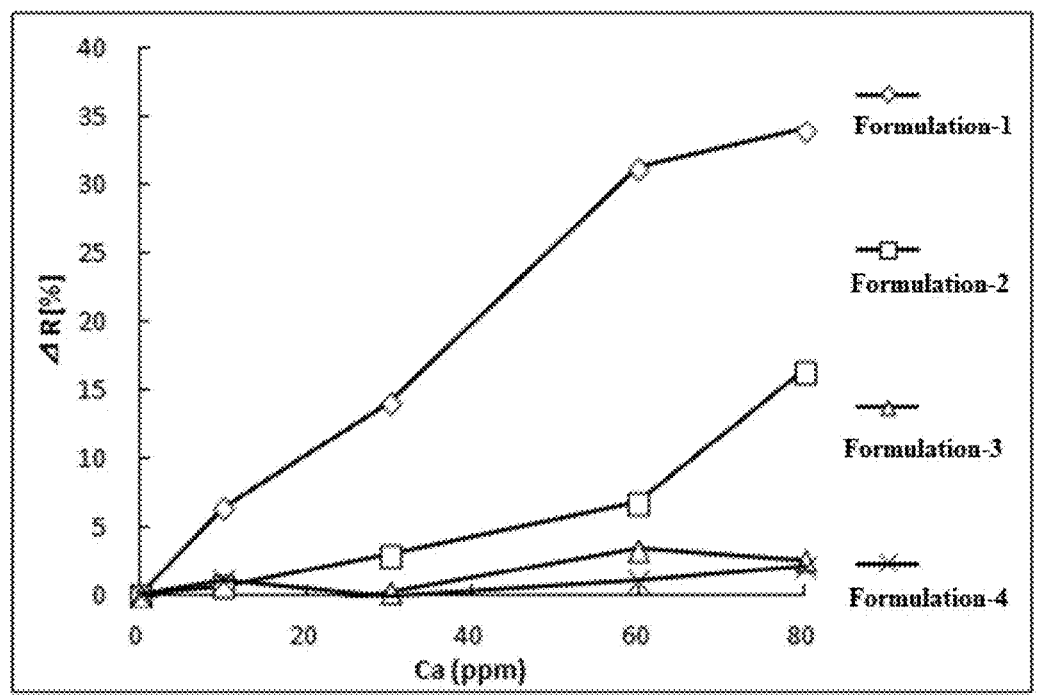
FIG. 3 is a graph illustrating the relationship between the calcium concentration and the measured value of ammonia in an ammonia measurement system (solid-phase reaction system) using glutamine synthetase. The measurement was carried out for each of addition of no EDTA, addition of 5 mM EDTA, addition of 10 mM EDTA, and addition of 20 mM EDTA.

The result is shown in FIG. 3. Although the measured value changed dependently on the calcium concentration, addition of EDTA improved the change in the reflectance (change in ΔR) caused by calcium.

TABLE 2

| Reagents | Formulation-1 | Formulation-2 | Formulation-3 | Formulation-4 |
|---|---|---|---|---|
| TES/NaOH pH = 8.0 (mM) | 150.00 | 150.00 | 150.00 | 150.00 |
| L-Glutamate (mM) | 150.00 | 150.00 | 150.00 | 150.00 |
| NAD+ (mM) | 15.00 | 15.00 | 15.00 | 15.00 |
| ATP (mM) | 15.00 | 15.00 | 15.00 | 15.00 |
| MgCl2 (mM) | 75.00 | 75.00 | 75.00 | 75.00 |
| EDTA (mM) | 0.00 | 5.00 | 10.00 | 20.00 |
| G6PDH (U/mL) | 80.00 | 80.00 | 80.00 | 80.00 |
| DI (U/mL) | 50.00 | 50.00 | 50.00 | 50.00 |
| ADP-HK (U/mL) | 30.00 | 30.00 | 30.00 | 30.00 |
| GST (U/mL) | 45.00 | 45.00 | 45.00 | 45.00 |
| Glucose (mM) | 25.00 | 25.00 | 25.00 | 25.00 |
| TV (mM) | 15.00 | 15.00 | 15.00 | 15.00 |

By the above test, it was found that inhibition of glutamine synthetase activity can be suppressed by adding a chelating agent to the reaction system of glutamine synthetase. In the example shown in Example 2, the test was carried out for measurement of ammonia. However, taking also the result of Example 1 into account, suppression of inhibition of the glutamine synthetase activity by addition of a chelating agent to the reaction system containing glutamine synthetase may be possible not only in cases of measurement of ammonia, but also in, for example, cases of measurement of ATP or glutamic acid.

While the invention has been described in detail with reference to exemplary embodiments thereof, it will be apparent to one skilled in the art that various changes may be made, and equivalents employed, without departing from the scope of the invention. Each of the aforementioned documents as well as JP2017-155476 is incorporated by reference herein in its entirety.

What is claimed is:

1. A method for carrying out glutamine synthetase reaction, consisting of carrying out glutamine synthetase reaction in a reaction system containing ammonia, adenosine triphosphate (ATP), L-glutamate and a chelating agent,
wherein the only enzymes used in the method are (i) glutamine synthetase; (ii) glutamine synthetase, ADP-dependent hexokinase and glucose-6-phosphate dehydrogenase; (iii) glutamine synthetase and ADP-dependent hexokinase; or (iv) glutamine synthetase and glucose-6-phosphate dehydrogenase
wherein the chelating agent is used to suppress the inhibition of glutamine synthetase activity by calcium.

2. The method according to claim 1, wherein the chelating agent is a compound containing not less than four carboxyl groups in its molecular structure.

3. The method according to claim 2, wherein the chelating agent is selected from the group consisting of ethylenediaminetetraacetic acid (EDTA), diethylene triamine-N,N,N',N'',N''-pentaacetic acid (DTPA), and trans-1,2-diaminocyclohexane-N,N,N',N'-tetraacetic acid (CyDTA).

4. A method for quantifying ammonia, comprising providing an ammonia-containing sample; carrying out glutamine synthetase reaction using the ammonia-containing sample by the method according to claim 1 to generate adenosine diphosphate (ADP); and quantifying ammonia based on the amount of ADP produced or the amount of reaction product produced from the ADP.

5. The method according to claim 4, said method further comprises:
    allowing glucose and ADP-dependent hexokinase to act on the ADP to produce glucose-6-phosphate,
    allowing glucose-6-phosphate dehydrogenase to act on the glucose-6-phosphate and an oxidized nicotinamide adenine dinucleotide (NAD) compound to produce a reduced NAD compound, and then
    quantifying the reduced NAD compound or the amount of reaction product produced from the reduced NAD compound.

6. The method of quantifying ammonia according to claim 5, said method further comprises: reacting a coloring agent with the reduced NAD compound to produce a pigment, and then quantifying the pigment to quantify ammonia.

7. The method according to claim 1, wherein the only enzymes used in the method are (ii) glutamine synthetase, ADP-dependent hexokinase and glucose-6-phosphate dehydrogenase.

8. The method according to claim 1, wherein the only enzymes used in the method are (iii) glutamine synthetase and ADP-dependent hexokinase.

9. The method according to claim 1, wherein the only enzymes used in the method are (iv) glutamine synthetase and glucose-6-phosphate dehydrogenase.

10. The method according to claim 1, wherein the only enzyme used in the method is (i) glutamine synthetase.

11. The method according to claim 1, wherein the method is carried out at a temperature of between about 45° C. to about 50° C.

12. The method according to claim 1, wherein the chelating agent is present in the reaction system at a concentration from 0.5 mM to 200 mM.

13. The method according to claim 1, wherein the chelating agent is present in the reaction system at a concentration from 5 mM to 20 mM.

14. The method according to claim 6, wherein the coloring agent comprises a tetrazolium compound.

15. The method according to claim 6, wherein the coloring agent comprises a tetrazolium compound selected from the group consisting of 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 2-(2-methoxy-4-nitrophenyl)-3-(4-nitrophenyl)-5-(2,4-disulfophenyl)-2H-tetrazolium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitrophenyl)-5-phenyl-2H-tetrazolium salt], 2,3-diphenyl-5-(4-chlorophenyl)tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, 2,5-diphenyl-3-(p-tolyl)tetrazolium salt, 2,3-diphenyl-5-(2-thienyl)tetrazolium salt, 2-benzothiazoyl-3-(4-carboxy-2-methoxyphenyl)-5-[4-(2-sulfoethylcarbamoyl)phenyl]-2H-tetrazolium salt, 2,2'-dibenzothiazoyl-5,5'-bis[4-di(2-sulfoethyl)carbamoylphenyl]-3,3'-(3,3'-dimethoxy-4,4'-biphenylene)ditetrazolium salt, 3-(4,5-dimethyl-2-thiazoyl)-2,5-diphenyl-2H-tetrazolium salt, 2,3-diphenyl-5-cyanotetrazolium salt, 2,3-diphenyl-5-carboxytetrazolium salt, 2,3-diphenyl-5-methyltetrazolium salt, 2,3-diphenyl-5-ethyltetrazolium salt, and 2-(4-Iodophenyl)-3-(2,4-dinitrophenyl)-5-(2,4-disulfophenyl)-2H-tetrazolium.

* * * * *